(12) United States Patent
Kim

(10) Patent No.: US 12,337,016 B2
(45) Date of Patent: Jun. 24, 2025

(54) COMPOSITION FOR PREVENTING OR TREATING OCULAR DISEASES COMPRISING AMNIOTIC EPITHELIAL CELL DERIVED EXOSOMES

(71) Applicant: KYUNGPOOK NATIONAL UNIVERSITY INDUSTRY-ACADEMIC COOPERATION FOUNDATION, Daegu (KR)

(72) Inventor: Hong Kyun Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 545 days.

(21) Appl. No.: 17/787,603

(22) PCT Filed: Mar. 22, 2021

(86) PCT No.: PCT/KR2021/003470
§ 371 (c)(1),
(2) Date: Jun. 21, 2022

(87) PCT Pub. No.: WO2021/230487
PCT Pub. Date: Nov. 18, 2021

(65) Prior Publication Data
US 2022/0409671 A1    Dec. 29, 2022

(30) Foreign Application Priority Data
May 12, 2020  (KR) ........................ 10-2020-0056647

(51) Int. Cl.
*A61K 35/50*  (2015.01)
*A61P 27/02*  (2006.01)

(52) U.S. Cl.
CPC .............. *A61K 35/50* (2013.01); *A61P 27/02* (2018.01)

(58) Field of Classification Search
CPC ................................ A61K 35/50; A61P 27/02
See application file for complete search history.

(56) References Cited

U.S. PATENT DOCUMENTS

2020/0289580 A1    9/2020  Rodriguez-Borlado et al.

FOREIGN PATENT DOCUMENTS

| JP | 2018-518534 A | 7/2018 |
| JP | 2019-508461 A | 3/2019 |
| KR | 10-2015-0039214 A | 4/2015 |

OTHER PUBLICATIONS

Supuran, (Expert opinion on therapeutic patents), 2019, vol. 29, No. 10,745-747).*
BlueCrossBlueShield of North caroluna, Corporate Medical Policy, 2016.*
International Search Report for PCT/KR2021/003470 mailed Jul. 20, 2021 from Korean Intellectual Property Office.
Kamiya, K. et al., Topical application of culture supernatant from human amniotic epithelial cells suppresses inflammatory reactions in cornea, Experimental Eye Research, 2005, vol. 80, pp. 671-679.
Harrell, C. R. et al., Therapeutic Potential of Mesenchymal Stem Cell-Derived Exosomes in the Treatment of Eye Diseases, Cell Biology and Translational Medicine, 2018, vol. 2. pages 47-57.
Kim, T.-H. et al., "Effects of conditioned media from human amniotic epithelial cells on corneal alkali injuries in rabbits", Journal of veterinary science, 2013, vol. 14, No. 1, pp. 61-67.
Zhao, B. et al., "Exosomal MicroRNAs Derived from Human Amniotic Epithelial Cells Accelerate Wound Healing by Promoting the Proliferation and Migration of Fibroblasts", Stem cells international, 2018, thesis No. 5420463, pp. 1-10.

* cited by examiner

*Primary Examiner* — Zohreh A Fay
(74) *Attorney, Agent, or Firm* — Revolution IP, PLLC

(57) ABSTRACT

The present invention relates to a composition comprising amniotic epithelial cell-derived exosomes as an active ingredient for prevention or treatment of ocular diseases and, more specifically, to a pharmaceutical composition for prevention or treatment of ocular diseases and a health functional food composition for prevention or alleviation of ocular diseases, each composition comprising amniotic epithelial cell-derived exosomes as an active ingredient. The amniotic epithelial cell-derived exosomes have ability to heal wounds on ocular tissues, recover the lacrimal gland destroyed by ocular diseases to induce lacrimation, and reduce the secretion of various inflammatory cytokines, thereby further effectively preventing or treating ocular diseases.

8 Claims, 11 Drawing Sheets

COMPOSITION FOR PREVENTING OR TREATING OCULAR DISEASES COMPRISING AMNIOTIC EPITHELIAL CELL DERIVED EXOSOMES

CROSS REFERENCE TO PRIOR APPLICATIONS

This application is the 35 U.S.C. 371 national stage of international application PCT/KR2021/003470 filed on Mar. 22, 2021 which claims priority to Korean Patent Application No. 10-2020-0056647 filed on May 12, 2020. The entire contents of each of the above-identified applications are hereby incorporated by reference.

TECHNICAL FIELD

The present disclosure relates to a composition including amniotic epithelial cell-derived exosomes as an active ingredient for prevention or treatment of ocular diseases.

BACKGROUND ART

Amniotic membrane is a thin biomembrane surrounding the fetus and serves as a barrier to protect the fetus against various infections and immune responses from the mother. Amniotic membrane is used for skin transplantation and various diseases. Amniotic membrane is composed of a simple cubical epithelium, a thick basement membrane, and an avascular mesenchymal stroma and does not show rejection even after transplantation so that amniotic membrane transplantation is being performed for ocular diseases. In addition, the amniotic membrane has been found to be able to maintain the growth and characteristics of corneal and conjunctival cells, inhibit epithelial apoptosis to promote epithelialization in the wound healing process, reduce inflammation, and inhibit apoptosis after wound healing by suppressing neovasularization. However, since amniotic membrane transplantation should be performed via a surgical method, complications such as surgical scar, bleeding, and infection may occur due to surgery, and there are limitations in repetitive transplantation. In order to overcome the shortcomings, eye drop treatment using some components of the amniotic membrane has been proposed.

Exosomes are one of extracellular vehicles, which are nano-sized endoplasmic reticulum surrounded by a lipid bilayer secreted by all cells out to the external environment. Exosomes are 50-200 nm luminal vesicles formed by internalization of the endosomal membrane in the process of maturation of multivesicular endosomes and secreted when the multivesicular endosomes combine with the cell surface. Exosomes contain various substances, such as proteins, lipids, nucleic acids, and metabolites, that exhibit biological activities, and reflect the state of the cells that they are derived from. Exosomes function as intercellular signaling substances secreted by cells and are known to play a role in intercellular communication by containing receptors and proteins as well as nuclear components. Since the bioactive molecules are contained, the physiologically active molecules are delivered upon fusion with a target cell, so that the physiologically active effect of a target cell may be easily induced. In addition, derived from cells, exosomes have low immunogenicity and the same membrane topology as cells, thereby being easily attached to the target cells.

Human-derived cellular exosomes are known to play an important role in angiogenesis, immunosuppression, and pathological stages of cancer and thus are attracting attention as excellent therapeutic candidates in the early stage of a disease.

Accordingly, the present disclosure is intended to develop a new therapeutic agent for an ocular disease using exosomes of the human-derived cells.

DISCLOSURE

Technical Problem

An object of the present disclosure is to provide a pharmaceutical composition for prevention or treatment of an ocular disease including exosomes of human-derived cells having excellent wound healing ability and anti-inflammatory effects as an active ingredient.

Another object of the present invention is to provide a health functional food composition for prevention or alleviation of an ocular disease including the exosomes as an active ingredient.

Technical Solutions

To achieve the above object, example embodiments of the present disclosure provide a pharmaceutical composition for prevention or treatment of an ocular disease including amniotic epithelial cell-derived exosomes as an active ingredient.

In addition, example embodiments of the present disclosure provide a health functional food composition for prevention or alleviation of an ocular disease including amniotic epithelial cell-derived exosomes as an active ingredient.

Advantageous Effects

Amniotic epithelial cell-derived exosomes according to example embodiments of the present disclosure have ability to heal wounds on ocular tissues, induce lacrimation by restoring lacrimal gland tissues destroyed by an ocular disease, and reduce the secretion of various inflammatory cytokines, thereby being able to be applied as a pharmaceutical composition and a health functional food composition for prevention or treatment of the ocular disease. Thus, it is possible to effectively prevent, alleviate, or treat the ocular disease by using the same.

BRIEF DESCRIPTIONS OF THE DRAWINGS

BEST MODE

Figure 1:
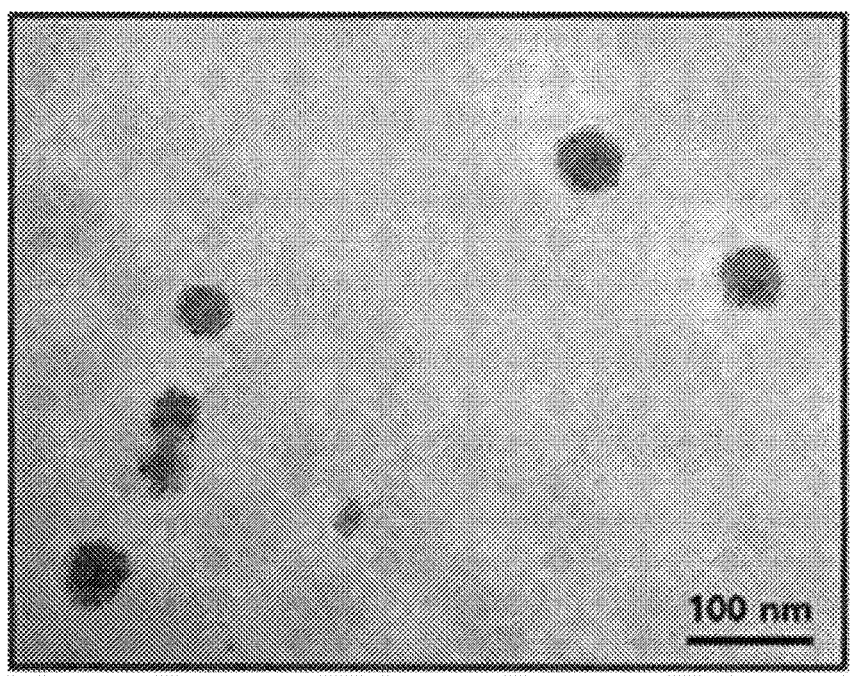
FIG. 1 is an image of amniotic epithelial cell-extracted exosomes according to an example embodiment of the present disclosure, observed with a transmission electron microscope (TEM).

Hereinafter, the present disclosure will be described in detail.

The present inventor has completed the present disclosure by obtaining amniotic epithelial cell-derived exosomes from the amniotic membrane donated by a mother and treating the same to dry eye syndrome-induced mice to observe the therapeutic effect of exosomes on ocular diseases, thereby confirming that the human amniotic epithelial cell-derived exosomes may be a new treatment strategy for ocular diseases.

The term "exosome" as used herein refers to all types of extracellular vehicles (EVs) surrounded by a membrane produced in the endosomal compartment of most eukaryotic cells to be produced extracellularly.

The term "prevention" as used herein refers to any action that suppresses development or delays the onset of ocular disease or at least one or more symptoms thereof, through administration of the pharmaceutical composition or the health functional food composition according to an example embodiment of the present disclosure. Also included is treatment of a subject in remission of the disease to prevent or avoid recurrence.

The term "treatment" as used herein refers to any action that improves or beneficially changes the symptoms, such as alleviation, reduction, or disappearance of ocular diseases or at least one or more symptoms thereof through administration of the pharmaceutical composition according to an example embodiment of the present disclosure.

In the present specification, the term "improvement" as used herein refers to any action that improves or beneficially changes the symptoms, such as alleviation, reduction, or disappearance of ocular diseases or at least one or more symptoms thereof through ingestion of the health functional food composition according to an example embodiment of the present disclosure.

The term "pharmaceutical composition" as used herein refers to a composition administered for a specific purpose, and for the purpose of the present disclosure, it means being administered in an attempt to prevent or treat ocular diseases or at least one or more symptoms thereof.

The term "health functional food" as used herein refers to food with high medical, clinical effects, which includes food manufactured and processed using raw materials or components having useful functionality for the human body according to Functional Foods for Health Act No. 6727, and is also processed to efficiently derive bioregulatory functions such as prevention of ocular diseases, body defense, immunity, and recovery for the purpose of the present disclosure in addition to nutrition supply.

An example embodiment of the present disclosure provides a pharmaceutical composition including amniotic epithelial cell-derived exosomes as an active ingredient for prevention or treatment of an ocular disease.

The "amniotic epithelial cell" is isolated from the amniotic epithelial tissues constituting the placenta and may have the characteristics of a pluripotent stem cell.

The "amniotic epithelial cell-derived exosome" may be included without limitation if it is an exosome obtainable from amniotic epithelial cells.

In the pharmaceutical composition according to an example embodiment of the present disclosure, the exosomes may have ability to heal wounds on corneal or conjunctival tissues.

The exosomes are able to restore the lacrimal gland tissues destroyed by ocular diseases such as dry eye syndrome, regulate goblet cells involved in the stabilization of the tear film, and induce lacrimation.

The "goblet cells" secrete mucus from the conjunctiva to maintain the stabilization of the tear film.

In addition, the exosome may reduce secretion of an inflammatory cytokine selected from the group consisting of interleukin 1 beta (IL-1β), interleukin 8 (IL-8), interleukin 6 (IL-6), interferon gamma (IFNγ), and tumor necrosis factor alpha (TNFα).

In the pharmaceutical composition according to an example embodiment of the present disclosure, the ocular disease may include an ocular surface disease and an intraocular disease, and more specifically, may be an ocular surface disease selected from the group consisting of dry eye syndrome, corneal epithelial damage, keratitis, conjunctivitis, and keratoconjunctivitis or an intraocular disease selected from the group consisting of endophthalmitis, uveitis, and macular degeneration, but is not limited thereto.

The pharmaceutical composition according to an example embodiment of the present disclosure may be prepared according to a conventional method in the pharmaceutical field. The pharmaceutical composition may be combined with a pharmaceutically acceptable, appropriate carrier depending on the formulation, and if necessary, may be prepared by further including excipients, diluents, dispersants, emulsifiers, buffers, stabilizers, binders, disintegrants, and solvents. The appropriate carrier does not deteriorate the activities and properties of the amniotic epithelial cell-derived exosomes according to an example embodiment of the present disclosure and may be selected differently depending on the administration type and formulation.

The pharmaceutical composition according to an example embodiment of the present disclosure may be applied in any formulation, and more specifically, be used by being formulated into oral dosage formulation, external preparations, suppositories, and parenteral dosage formulation for sterile injection solutions according to conventional methods.

Preferably, the composition may be any one formulation selected from the group consisting of eye drops, injections, granules, tablets, pills, capsules, gels, syrups, suspensions, emulsions, drops, and solutions.

A solid formulation among the oral dosage formulations is in the form of granules, tablets, pills, capsules, and discutients to be prepared by mixing at least one or more excipients such as starch, calcium carbonate, sucrose, lactose, sorbitol, mannitol, cellulose, and gelatin, and lubricants such as magnesium stearate and talc may be included in addition to simple excipients. In addition, the capsule formulation may further include a liquid carrier such as fatty oil in addition to the above-mentioned substances.

A liquid formulation among the oral dosage formulations may be suspensions, solutions, emulsions, and syrups, and various excipients such as wetting agents, sweeteners, fragrances, and preservatives may be included in addition to water and liquid paraffin, which are commonly used simple diluents.

As the parenteral formulation, sterile aqueous solutions, non-aqueous solvents, suspensions, emulsions, freeze-dried formulations, eye drops, drop solutions, injections, and suppositories may be included. As the non-aqueous solvents and suspensions, propylene glycol, polyethylene glycol, vegetable oils such as olive oil, and injectable esters such as ethyl oleate may be used. Witepsol, macrogol, Tween 61, cacao butter, laurin fat, and glycerogelatin may be used as a base of the suppositories. Any appropriate agent known in the art may be used while it is not limited thereto.

In the pharmaceutical composition according to an example embodiment of the present disclosure, the pharmaceutical composition may be administered in a pharmaceutically effective amount.

The term "pharmaceutically effective amount" as used herein refers to an amount sufficient to treat a disease at a reasonable benefit/risk ratio applicable to medical treatment while not causing side effects.

The effective dose level of the pharmaceutical composition may be differently determined depending on the purpose of use, the age, sex, weight and health status of a patient, the type of disease, the severity, the activity of a drug, the sensitivity to a drug, an administration method, administration duration, administration route and excretion rate, a treatment period, elements including drugs blended or used in combination with, and other factors well known in the medical field. For example, although not constant, generally 0.001 to 100 mg/kg, preferably 0.01 to 10 mg/kg, may be administered once to several times a day. The above dosage does not limit the scope of the present disclosure in any way.

The pharmaceutical composition according to an example embodiment of the present disclosure may be administered to any animal in which an ocular disease may be developed, and the animal may include, for example, not only humans and primates, but also livestock such as cattle, pigs, horses, and dogs.

The pharmaceutical composition according to an example embodiment of the present disclosure may be administered in an appropriate administration route depending on the type of the formulation and may be administered via various routes, either oral or parenteral as long as it is able to reach a target tissue. The administration method is not particularly limited and may be conducted in a conventional methods such as oral, intraocular, rectal or intravenous, muscle, skin application, respiratory inhalation, intrauterine dura mater or intracere-broventricular injection.

The pharmaceutical composition according to an example embodiment of the present disclosure may be used alone for the prevention or treatment of ocular diseases or be used in combination with surgery or other drug treatment.

An example embodiment of the present disclosure provides a health functional food composition including amniotic epithelial cell-derived exosomes as an active ingredient for prevention or alleviation of ocular diseases.

The exosomes have ability to heal wounds on the corneal or conjunctival tissues, may restore the destroyed lacrimal gland tissues, regulate goblet cells involved in the stabilization of the tear film, and induce lacrimation. In addition, the exosome may reduce the secretion of an inflammatory cytokine selected from the group consisting of IL-1β, IL-8, IL-6, IFNγ, and TNFα, and thus may be used as a health functional food composition for the prevention or alleviation of ocular diseases.

Corresponding features may be substituted for the above-mentioned parts.

In the health functional food composition according to an example embodiment of the present disclosure, the health functional food may be prepared in the form of powder, granules, tablets, capsules, syrups, or beverages for prevention or alleviation of ocular diseases. There is no limitation in the form that the health functional food may take, and the health functional food may be formulated in the same way as the pharmaceutical composition so as to be used as a functional food or added to various foods.

In the health functional food composition according to an example embodiment of the present disclosure, the health functional food may include all foods in a conventional sense. For example, beverages and various drinks, fruits and processed foods thereof (canned fruit and jam), fish, meat and processed foods thereof (ham and bacon), breads and noodles, cookies and snacks, and dairy products (butter and cheese) are possible, and all functional foods in a conventional sense may be included. Food used as feed for animals may also be included.

The health functional food composition according to an example embodiment of the present disclosure may be prepared by further including food additives acceptable in food science and other appropriate auxiliary components commonly used in the art. The suitability as the food additive may be determined by the standards and criteria related to corresponding items according to the general rules and general test methods of Korean Food Additives CoDEX approved by the Ministry of Food and Drug Safety, unless otherwise stipulated. The items listed in the "Korean Food Additives CoDEX" may include, for example, chemical compounds such as ketones, glycine, calcium citrate, nicotinic acid, and cinnamic acid; natural additives such as persimmon pigments, licorice extracts, crystalline cellulose, kaoliang color, and guar gum; and mixed preparations such as sodium L-glutamate preparations, noodle-added alkali agents, preservative preparations, and tar color preparations.

The other auxiliary components may additionally include, for example, flavoring agents, natural carbohydrates, sweeteners, vitamins, electrolytes, coloring agents, pectic acid, alginic acid, organic acids, protective colloidal thickeners, pH adjusting agents, stabilizers, preservatives, glycerin, alcohols, and carbonating agents. In particular, monosaccharides such as glucose and fructose, disaccharides such as maltose and sucrose, polysaccharides such as DEXtrin and cycloDEXtrin, and sugar alcohols such as xylitol, sorbitol, and erythritol may be used as the natural carbohydrate, and natural sweeteners such as thaumatin and stevia extracts or synthetic sweeteners such as saccharin and aspartame may be used as the sweetener.

The effective dose of the amniotic epithelial cell-derived exosomes contained in the health functional food according to an example embodiment of the present disclosure may be appropriately adjusted depending on the purpose of use thereof, such as prevention or alleviation of ocular diseases.

The health functional food composition causes no side effects that may occur during long-term administration of general drugs by using food as a raw material and may be taken as an adjuvant for prevention or alleviation of ocular diseases due to excellent portability.

MODES FOR CARRYING OUT INVENTION

Hereinafter, examples will be described in detail to help the understanding of the present disclosure. However, the following examples are merely illustrative of the content of the present disclosure, and the scope of the present disclosure is not limited to the following examples. The examples of the present disclosure are provided to more completely explain the present disclosure to those skilled in the art.

Example 1

Isolation and Culture of Human Amniotic Epithelial Cells and Exosome Extraction The placenta removed by cesarean hysterectomy from a complication-free pregnant woman was placed in a sterile container and washed with physiological saline to remove blood clots. An incision was made from an umbilical cord side using medical scissors, and the amniotic membrane was peeled off little by little by inserting forceps from the chorion. After spreading the removed amniotic membrane with the epithelium facing down on a stainless-steel plate, the remaining chorion and blood clots were removed by hand rubbing and washed with physiological saline five times repeatedly. After spreading the amniotic membrane with the epithelium facing down on the stainless-steel plate, the amniotic membrane was attached to nitrocellulose paper (NC paper, 0.45 μ) by covering with the NC paper. After attachment, it was cut into a square size of about 5-10 cm, placed in a container containing Hank's balanced salt solution (HBSS), and transferred to the laboratory.

The isolated amniotic membrane was transferred to a sterile beaker and washed several times using HBSS to completely remove residual blood and tissue debris. The amniotic membrane piece was then incubated for 10 minutes at 37° C. using PBS containing 0.5 mM of ethylenediaminetetraacetic acid (EDTA) and penicillin-streptomycin. After that, the amniotic membrane piece was left at 37° C. with a 0.05% trypsin/EDTA solution for 5 minutes, the solution was discarded to remove the residue, and the culture medium was collected after a reaction carried out by intermittently shaking with a new 0.05% trypsin/EDTA solution at 37° C. for 10 minutes. Trypsin/EDTA was inactivated by adding four times the volume of DMEM/F12 culture medium, centrifuged at 300×g for 10 minutes, and filtered through a cell strainer with a pore size of 100 μm after suspension, followed by centrifugation and counting.

The isolated cells were seeded in a poly-L-lysine-coated culture dish at a density of $1.2 \times 10^5 / cm^2$ using DMEM/F12 (10% FBS, 1% P/S) culture medium, and cultured at 37° C. under 5% $CO_2$ conditions after being seeded. If necessary, culture was conducted by adding 10 ng/ml of an epidermal growth factor (EGF), a Rho-associated coil kinase (ROCK) inhibitor, and a leukemia inhibitory factor (LIF).

The exosome may be extracted with various methods such as an isolation method via phosphatidylserine binding, an antibody binding isolation method, and an ultra-high-speed centrifugation.

1) Extraction of Exosomes Using Ultra-High-Speed Centrifugation

Amniotic epithelial cells were grown to meet 80% confluence in a culture dish coated with DMEM/F12 (10% FBS, 10 ng/ml EGF, 1% P/S) poly-L-lysine, and cells were washed with PBS three times so as to remove all the remaining medium. The medium was replaced with DMEM/F12 (1% exosome free FBS, 10 ng/ml EGF, 1% P/S) medium, and 72 hours later, the conditioned medium was collected. Centrifugation was performed at 300×g for 10 minutes to remove cell debris, and the supernatant obtained after the centrifugation was collected and centrifuged at 1500×g for 30 minutes. The supernatant obtained after the centrifugation was collected, and the conditioned medium was concentrated using a centrifugal concentrator (100,000 MWCO memebrane; Corning). The concentrated conditioned medium was ultracentrifuged at 100,000×g for 2 hours, and the pellet obtained thereby was resuspended in PBS and then ultracentrifuged again at 100,000×g for 2 hours. Exosomes were included in the final pellet which is then subjected to resuspension in PBS to be used immediately or stored at 4° C. until use.

2) Isolation Method Via Phosphatidylserine Binding

Amniotic epithelial cells were cultured to meet 80% confluence in a DMEM/F12 (10% FBS, 10 ng/ml EGF, 1% P/S) poly-L-lysine-coated culture dish, and washed with PBS three times to remove all the remaining medium. The medium was replaced with DMEM/F12 (1% Exosome Free FBS, 10 ng/ml EGF, 1% P/S) medium, and the conditioned medium was collected 72 hours later. After centrifugation at 300×g for 5 minutes to remove cells remaining in the medium, the supernatant was collected and centrifuged at 1,200×g for 20 minutes to remove cell debris that might remain. Finally, centrifugation of the supernatant at 10,000×g for 30 minutes had large extracellular vesicles and exosomes separated, making the exosomes to be included in the supernatant of the finally centrifuged conditioned medium.

The collected supernatant was prepared by concentrating the same up to 50 times using a centrifugal concentrator (100,000 MWCO memebrane; Corning) and stored at 4° C. until use. Exosomes were isolated from the concentrated supernatant using a phosphatidyl binding isolation kit (MagCapture™ Exosome Isolation Kit PS, Wako).

The MagCapture method is an exosome isolation method via phosphatidylserine (PS) binding and enables isolation of exosomes that bind to exosome captures to which magnetic beads are bound without using an antibody. Briefly, streptavidin magnetic beads included in the kit are diluted in an exosome capture immobilizing buffer and reacted on a magnetic stand for 1 minute, thereby leaving the beads only. Herein, biotin-labeled exosome captures were added followed by treatment at 4° C. for 10 minutes using a rotator, and then a reaction was carried out for 1 minute on the magnetic stand to prepare exosome capture immobilized beads.

A sample was prepared by adding an exosome binding enhancer (×500) in a volume ratio of 1:500 to the concentrated conditioned medium and reacted with the exosome capture immobilized beads using the rotator at 4° C. for 3 hours or more, thereby isolating EVs-bound beads only using the magnetic stand.

The EVs-bound beads were washed with a wash buffer containing the exosome binding enhancer, leaving only the EVs-bound beads using the magnetic stand. By adding an exosome elution buffer to the EVs-bound beads, magnetic beads and exosomes were eluted to finally obtain exosomes. The obtained exosomes were resuspended in PBS to be used immediately or stored at −80° C. until use.

Figure 2:
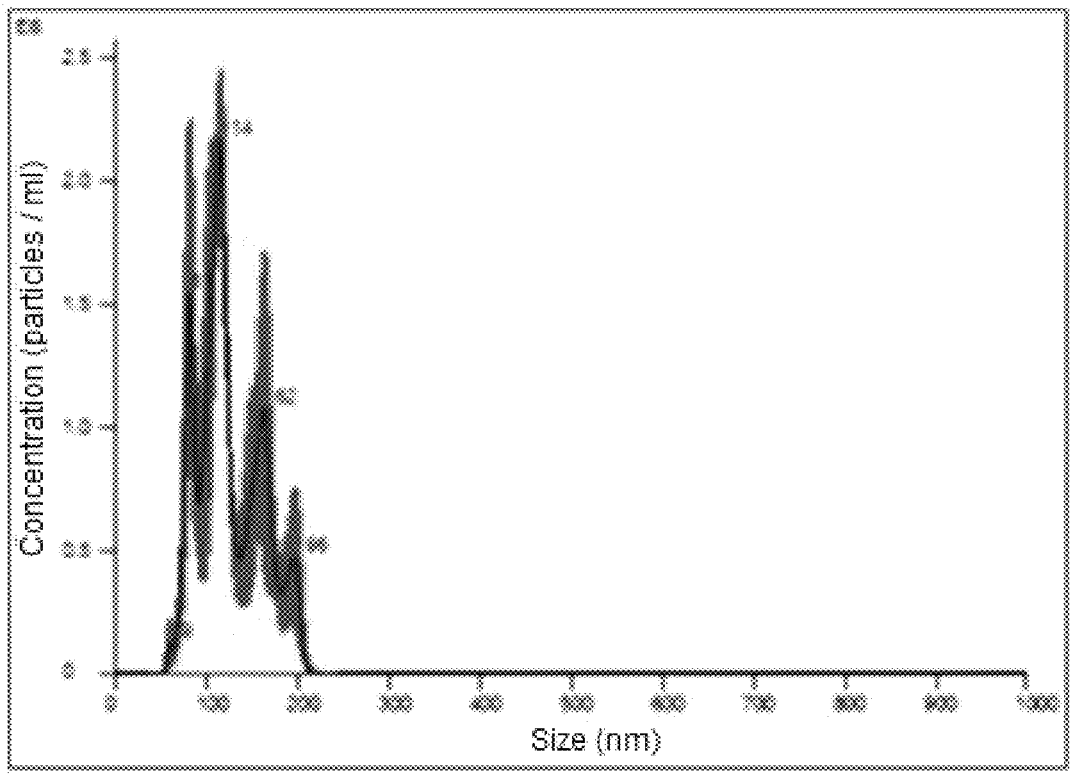
FIG. 2 is a result of measuring the size and polydispersity of exosomes according to FIG. 1.

FIG. 1 is an image of exosomes extracted from amniotic epithelial cells according to an example embodiment of the present disclosure observed using a transmission electron microscope (TEM), and FIG. 2 is a result of measuring the size and polydispersity of exosomes according to FIG. 1 using NanoSight (Malvern zetasizer, Worcestershire, UK), wherein exosomes with a size of 50-200 nm were measured.

Figure 3:
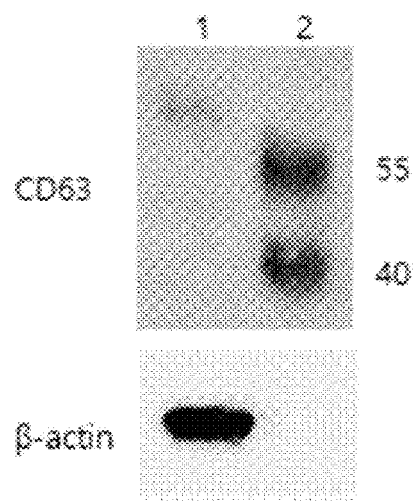
FIG. 3 shows identification of exosomes using Western blotting.

FIG. 3 is identification of exosomes using Western blotting, wherein amniotic epithelial cell-derived exosome pellets were suspended in a cell lysis buffer, and the amniotic epithelial cell lysates were used as a control group. The lysate was boiled in a sodium dodecyl sulfate (SDS) loading dye for 5 minutes and electrophoresed in 10% SDS-polyacrylamide gel electrophoresis (PAGE), and then proteins were transferred to an NC membrane. After a reaction with 5% skim milk for 1 hour, amniotic epithelial cell-derived exosomes were identified by treatment with CD63 antibody.

As a result, the stable isolation of human amniotic epithelial cell-derived exosomes was confirmed.

Experimental Example 1

Cell Proliferation Analysis

A human conjunctival cell line was dispensed in a 96-well plate to be grown to take 60% of a plate area, cultured for 16 hours in a culture medium in the absence of growth factors and FBS, and treated with 70 mM of NaCl to induce an environment similar to dry eye syndrome.

After amniotic epithelial cell-derived exosomes were treated with 0, 300, 600, and 3000 particles per cell respectively and cultured for 24 hours, the medium was removed, 20 μL of methylthiazol tetrazolium (MTT) was added to each well, and culture was conducted at 37° C. for 3 hours to determine cell proliferation.

Figure 4:
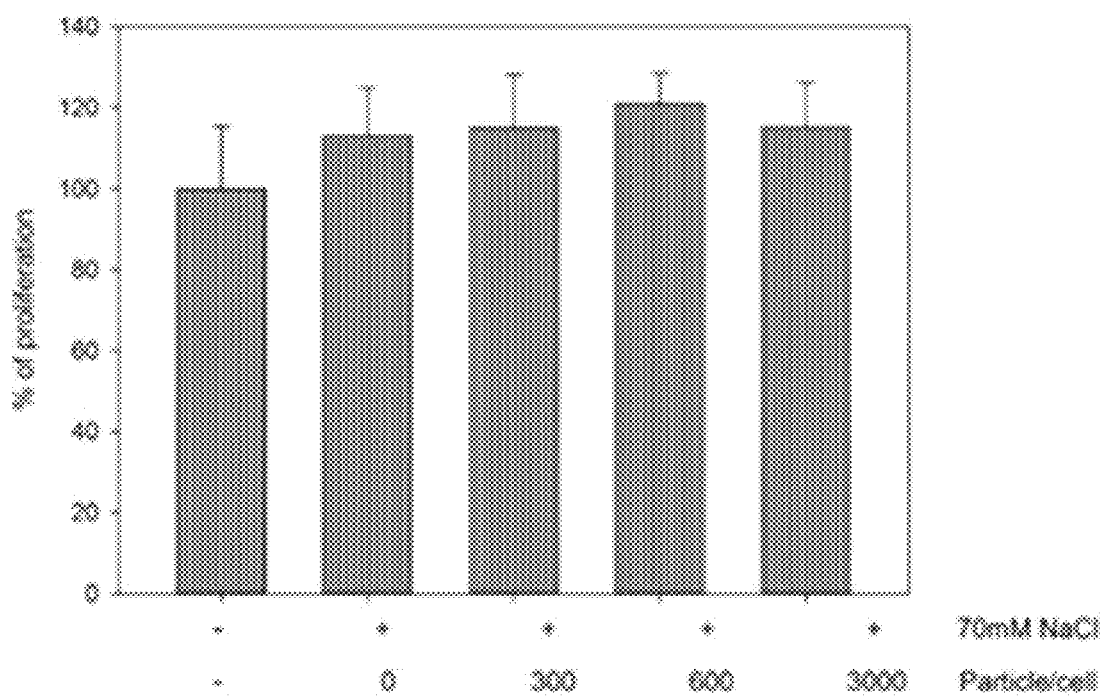
FIG. 4 shows determination of an effect of human conjunctival cell line proliferation upon exosome treatment.

As a result, stable proliferation of human conjunctival cell lines was observed even after treatment with each concentration of exosomes, as shown in FIG. 4. As a result, it was confirmed that cell proliferation inhibition or cytotoxicity due to the exosome treatment did not appear.

Experimental Example 2

Analysis of Endocytosis of Exosomes into Human Conjunctival Epithelial Cells

In order to confirm the endocytosis of the exosomes into the epithelial cells, staining with a red fluorescent dye (Dil, Thermo Fisher) was performed. Exosomes and $1\times10^{-3}$ mM Dil were reacted at 37° C. for 30 minutes and diluted in 100 μL of PBS to be used immediately. When the cells were grown to meet 60% confluence on a cell culture plate using the human conjunctival epithelial cell line, the medium was replaced with a 1% exosome-free medium and then treated with Dil-stained exosomes to be grown at 37° C. in the presence of 5% $CO_2$ for 4 hours.

Figure 5:
FIG. 5 is a result of checking of the state in which exosomes are internalized into the human conjunctival epithelium.

As a result, the endocytosis of the Dil-labeled exosomes into human conjunctival epithelial cells was found as shown in FIG. 5.

Example 3

Analysis of IL-8 Concentration Change

The human conjunctival cell line was dispensed in a 96-well plate, grown to take 80% of the plate area, and treated with 70 mM of NaCl to induce an environment similar to dry eye syndrome.

Amniotic epithelial cell-derived exosomes were treated with 60, 300, and 600 particles per cell respectively and cultured for 24 hours to check the change in the concentration of IL-8 released out of the cell. The control group was not treated with the exosomes. After collecting the medium used for cell culture, ELISA was performed using the LEGEND MAX™ Human IL-8 ELISA kit with Pre-coated Plates (Biolegend, San Diego, CA, USA) according to the manufacturer's protocol.

Figure 6:
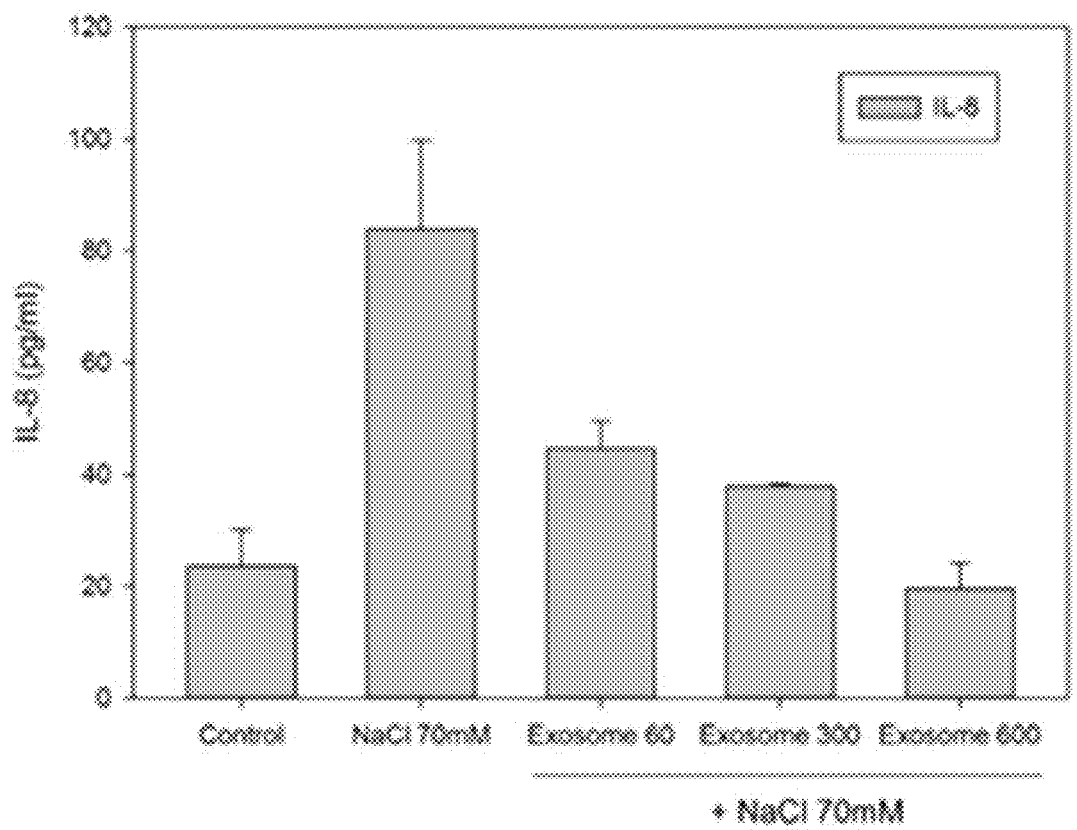
FIG. 6 is a result of checking the changes in the concentration of IL-8 upon the exosome treatment.

As a result, as shown in FIG. 6, in the case that the exosomes were treated in a cell culture environment that the dry eye syndrome-like environment was induced, it was confirmed that the concentration of IL-8 was decreased compared to the control group not treated with the exosomes.

Example 4

Analysis of Wound Healing

Whether the amniotic epithelial cell-derived exosomes affect the in-vitro wound healing ability was confirmed by culturing the human conjunctival cell line.

Specifically, when a confluent monolayer was formed by culturing the human conjunctival cell line in a 96-well cell culture plate inside an incubator for 24 hours, starvation state was maintained with replacement of 1% exosome serum-free medium for 4 hours, and then wounds were formed using a wound forming tool (WoundMaker; Essen BioScience, Inc., USA).

The amniotic epithelial cell-derived exosomes were treated with 300 particles per cell and observed for 48 hours via IncuCyte (Essen BioScience, Inc., Michigan, USA) to measure the cell wound healing ability.

Figure 7:
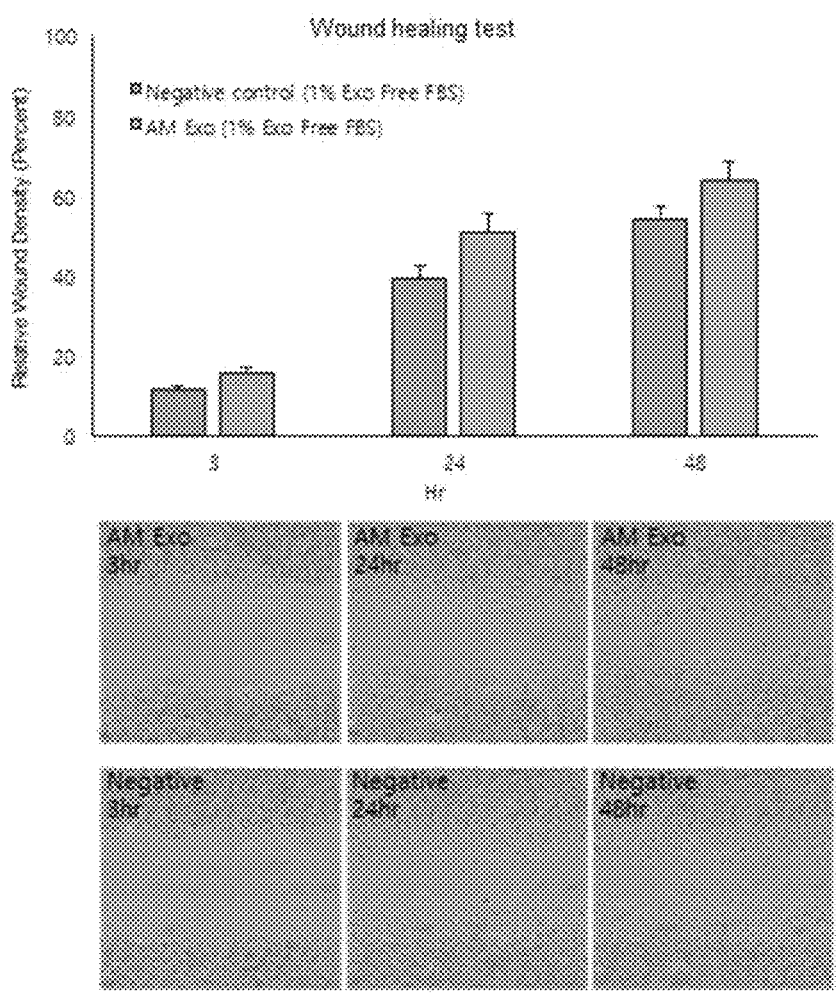
FIG. 7 is results of determining the wound healing ability upon the exosome treatment.

As a result, as shown in FIG. 7, there was a significant difference between the group treated with the amniotic epithelial cell-derived exosomes and the control group. It was confirmed that the wound healing ability increases in the group treated with the amniotic epithelial cell-derived exosomes than the control group not treated with the exosomes.

Experimental Example 5

Measurement of Lacrimation in an Animal Model with Dry Eye Syndrome

1. Animal Model with Dry Eye Syndrome

Male BABL/c mice aged 8-12 weeks were bred in a pathogen-free place with a cap at the top of a filter while access to food is allowed freely. A scopolamine patch (Kimite, Myungmoon Pharmaceutical Co., Ltd., Korea) was attached to mice for 9 days, and the mice were bred in an environment-controllable chamber (18.5±5% average humidity, 23° C.±2.5° C., 20 L/min wind speed) while being exposed to scopolamine at a concentration of 0.25 mg/day so as to create a dry stress. After the termination of exposure to the scopolamine, the mice were managed under a normal breeding environment (60±10% average humidity, 23° C.±2.5° C.).

2. Treatment of Amniotic Epithelial Cell-Derived Exosomes

Amniotic epithelial cell-derived exosomes at concentrations of 0.1 μg (Exo.1) and 1 μg (Exo.2) and 10 μM of dexamethasone (DEX) were treated to mice having corneal wounds formed due to exposure to the scopolamine patch and dry stress. Treatment was performed three times a day in a volume of 5 μl each for a single dose and lasted for up to 14 days. The control group was treated with normal saline (NS) three times a day in a volume of 5 μl each for a single dose.

3. Lacrimation Measurement Experiment

Mice exposed to the scopolamine patch and dry stress for 10 days were treated with NS, DEX, Exo.1, and Exo.2 for up to 14 days, and tear production was measured on days 0, 3, 7, and 14.

Measurement was conducted for 60 seconds after placing a phenol red-impregnated cotton thread on the lateral cantus of the mouse eyeball. The thread wet with tears turned red, and the length changed thereby was measured to be evaluated.

Figure 8:
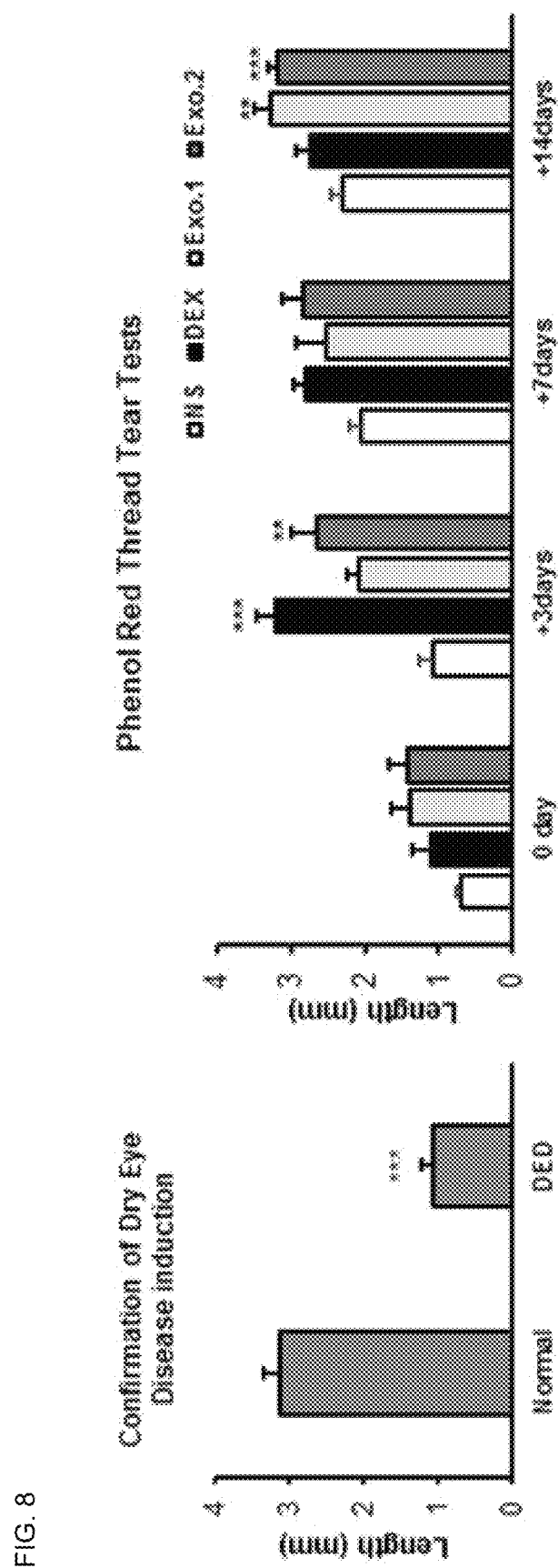
FIG. 8 shows results of checking the change in the amount of tear secretion upon the exosome treatment in an animal model with dry eye syndrome.

As a result, as shown in FIG. 8, the dry eye syndrome-induced mice showed decreased lacrimation, and lacrimation was induced in the exosome-treated mice induced with dry eye syndrome. Compared with DEXamethasone, which is used as a treatment for dry eye syndrome, favorable effects were observed in the exosome-treated group when administered for more than 14 days.

Experimental Example 6

Analysis of Corneal Lissamine Green Staining in Animal Model with Dry Eye Syndrome Mice exposed to the scopolamine patch and dry stress for 10 days were treated with NS, DEX, Exo.1, and Exo.2 for up to 14 days, and corneal staining was performed using lissamine green used to diagnose dry eye syndrome on days 0, 3, 7, and 14.

Staining was performed using lissamine green ophthalmic strips (optitech), followed by confirmation with a slit lamp microscope (Model 900 BQ; Switzerland). Corneal lissamine green staining was scored from 0 to 5 according to the Oxford Scheme grading system (2003, Grading Of Corneal and Conjunctival Staining in the Context of Other Dry Eye Tests.). In the absence of staining, a grade of 0 was given, with a maximum score of 5.

Figure 9:
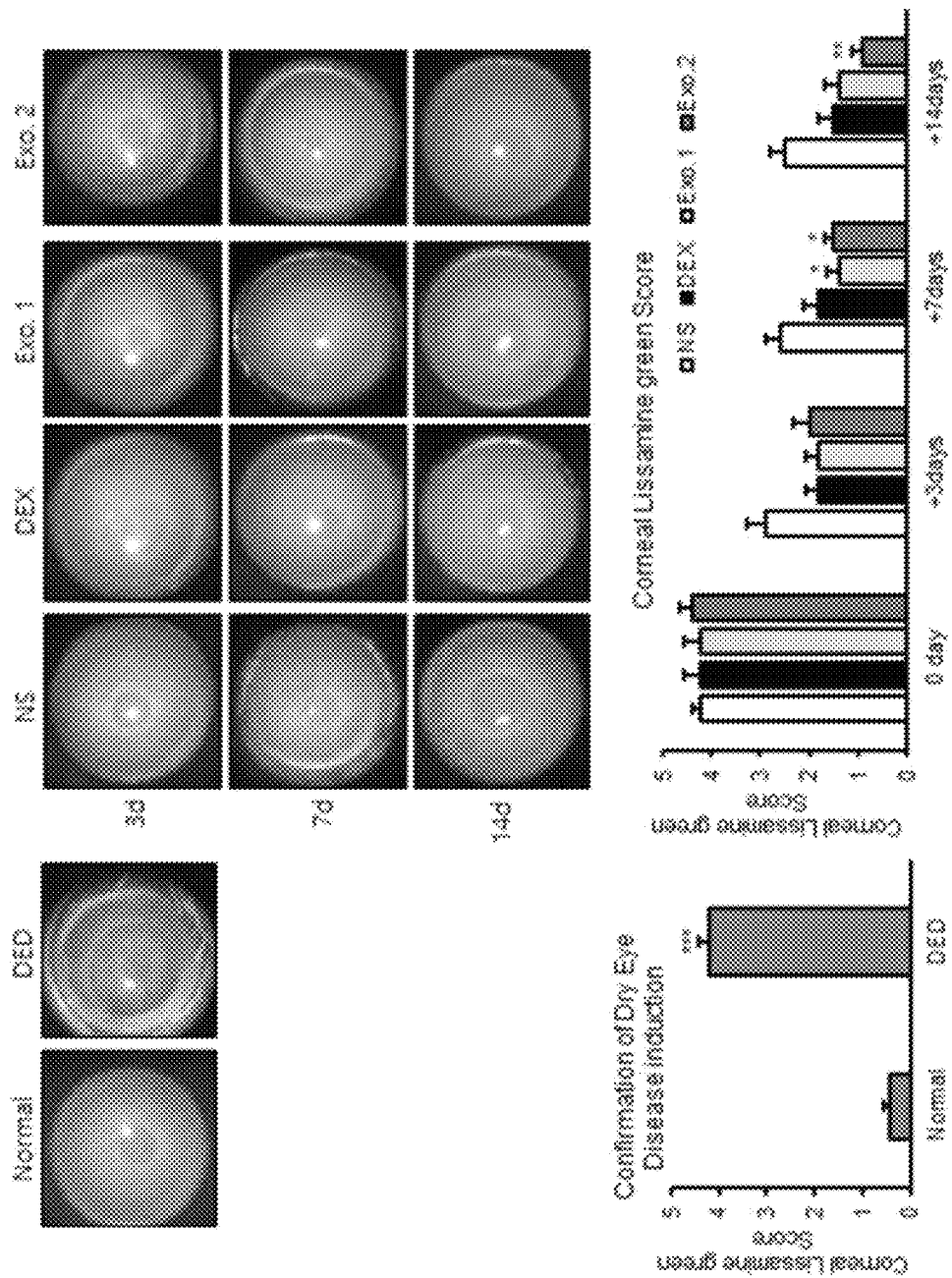
FIG. 9 is a result of performing corneal staining with lissamine green in an animal model with dry eye syndrome.

As a result, as shown in FIG. 9, although normal mice were barely stained with lissamine green, the corneal surface of mice induced with dry eye syndrome showed a high degree of staining with lissamine green. In the case of mice treated with exosomes after induction of dry eye syndrome, the degree of staining with lissamine green was lower than that of the experimental group solely treated with NS. Compared with DEX, which is used as a treatment for dry eye syndrome, favorable effect was observed in the exosome-treated mouse group when administered for 7 days or more.

Experimental Example 7

Analysis of Periodic Acid Schiff (PAS) Staining of Conjunctival Tissues in an Animal Model with Dry Eye Syndrome Mice exposed to the scopolamine patch and dry stress for 10 days were treated with NS, DEX, Exo.1, and Exo.2 for up to 14 days and sacrificed on days 0, 3, 7, and 14 to collect the conjunctival tissues. The obtained conjunctival tissues were immobilized in 10% formalin and embedded in paraffin. Tissues were cut to a thickness of 7 μm to prepare unstained slides, and periodic acid Schiff (PAS) staining was performed. PAS staining was performed on conjunctival goblet cells using a commercially available kit (Merck, Darmstadt, Germany) according to the manufacturer's instructions, and the stained portion was photographed with an optical microscope. In goblet cells, glycoprotein and glycogen, which are the main components in the mucin synthesis, were stained red by PAS staining, and the cells were counted to measure the goblet cell density based on the number of goblet cells per 100 μm.

Figure 10:
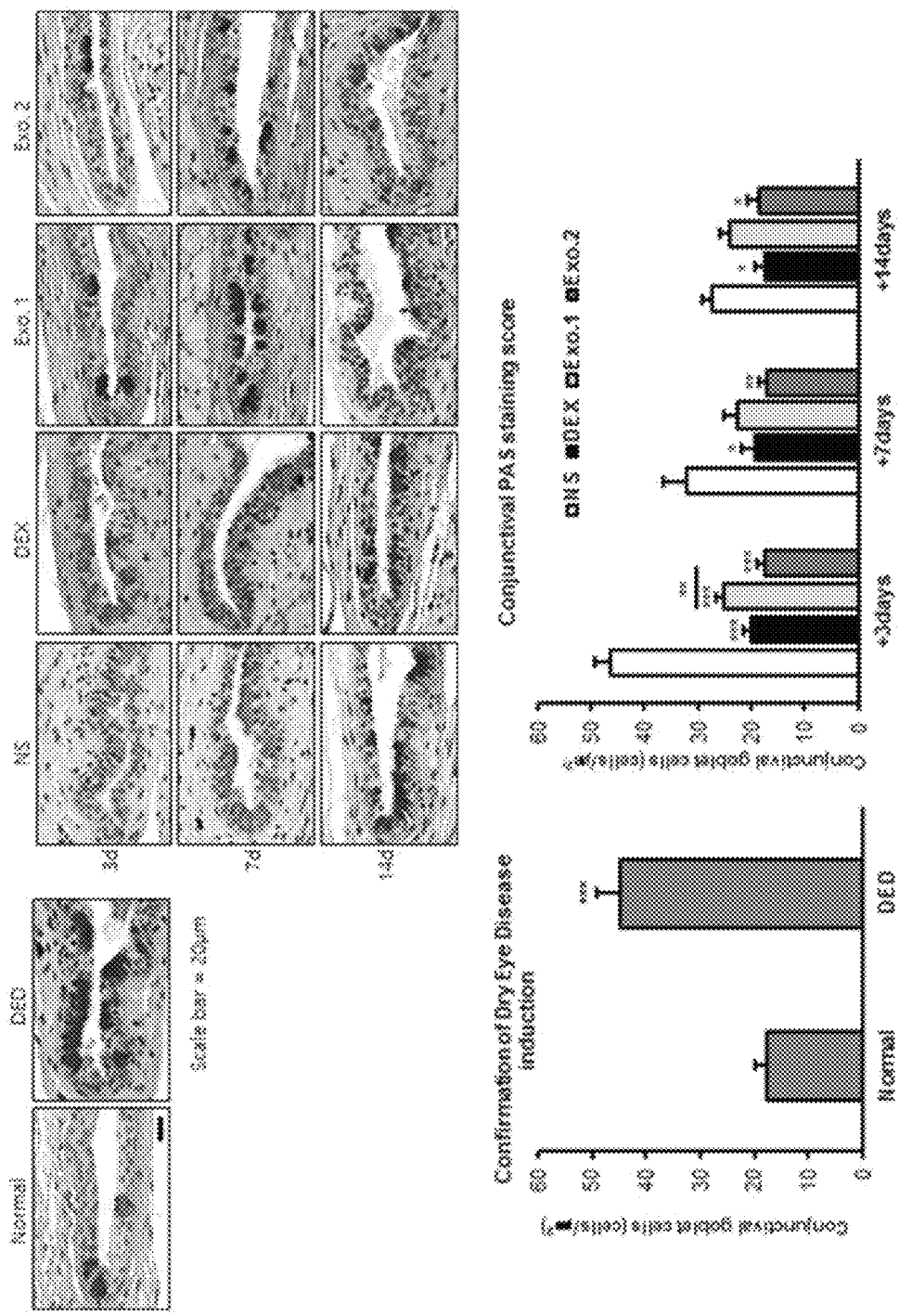
FIG. 10 shows results of performing periodic acid Schiff (PAS) staining of conjunctival tissues in an animal model with dry eye syndrome.

As a result, as shown in FIG. 10, it was found that dry eye syndrome-induced mice were affected by the distribution of glycoprotein and glycogen, which are the main components in the mucin synthesis in the conjunctival goblet cells. The number of goblet cells detected by PAS staining in the dry eye syndrome-induced mice was more than twice that of normal mice. In mice treated with exosomes after induction of dry eye syndrome, the number of goblet cells was reduced, and compared to DEX used as a treatment for dry eye syndrome, exosomes (Exo.2) at a concentration of 1 μg were as effective as DEX.

Experimental Example 8

Analysis of Alcian Blue Staining of Lacrimal Gland Tissues in an Animal Model with Dry Eye Syndrome Mice exposed to the scopolamine patch and dry stress for 10 days were treated with NS, DEX, Exo.1, and Exo.2 for up to 14 days and sacrificed on days 0, 3, 7, and 14 to collect the lacrimal gland tissues. The obtained lacrimal gland tissues were immobilized in 10% formalin and embedded in paraffin. Tissues were cut to a thickness of 7 μm to prepare unstained slides, alcian blue staining was performed, and the stained portion was photographed with the optical microscope.

Figure 11:
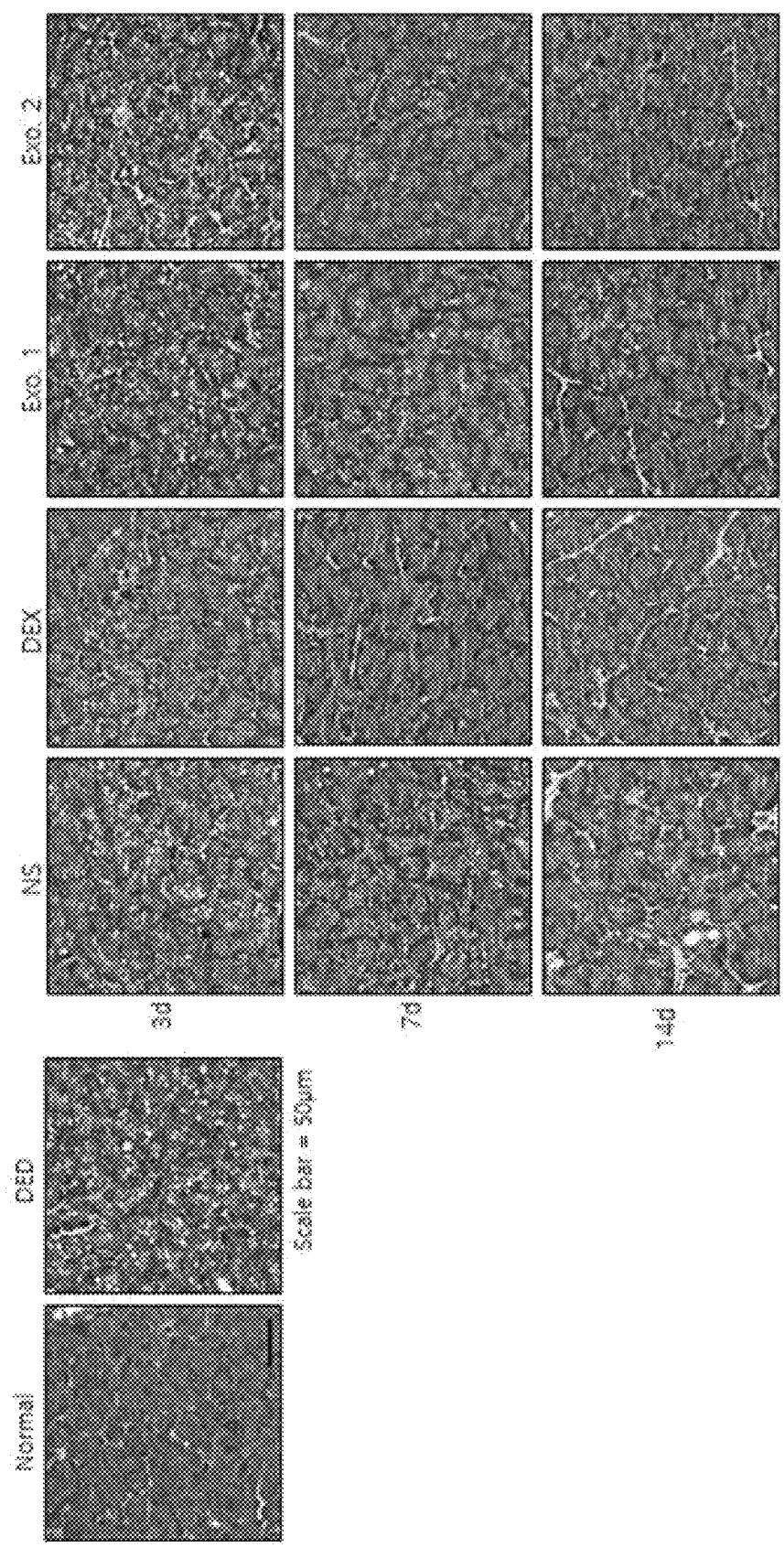
FIG. 11 shows results of performing alcian blue staining of lacrimal gland tissues in an animal model with dry eye syndrome.

As a result, as shown in FIG. 11, it was confirmed that the significant portion of the acinus structure of the lacrimal gland was destroyed in the lacrimal gland of the dry eye syndrome-induced mouse, and it was also confirmed that recovery took place with the treatment of DEX and exosomes. It is considered that exosomes affect the maintenance of lacrimal gland structure and function of glands.

Experimental Example 9

Confirmation of Changes in the Cytokine Secretion in Corneal Tissues of an Animal Model with Dry Eye Syndrome Total RNA was extracted from mouse corneal tissues using the Reliaprep™ RNA extraction system (Promega, Fitchburg, WI, USA). The tissues were washed with cold PBS and RNA extraction was performed according to the manufacturer's instructions. cDNA was synthesized using a cDNA reverse transcription kit (Applied Biosystems, Waltham, MA). To determine the expression of cytokines in mouse cornea, real-time PCR was performed using Power SYBR Green PCR Master Mix (Applied Biosystems, CA, USA) and StepOnePlus™ Real-time PCR system (Applied Biosystems, CA, USA). The PCR reaction was performed according to the manufacturer's protocol.

Figure 12:
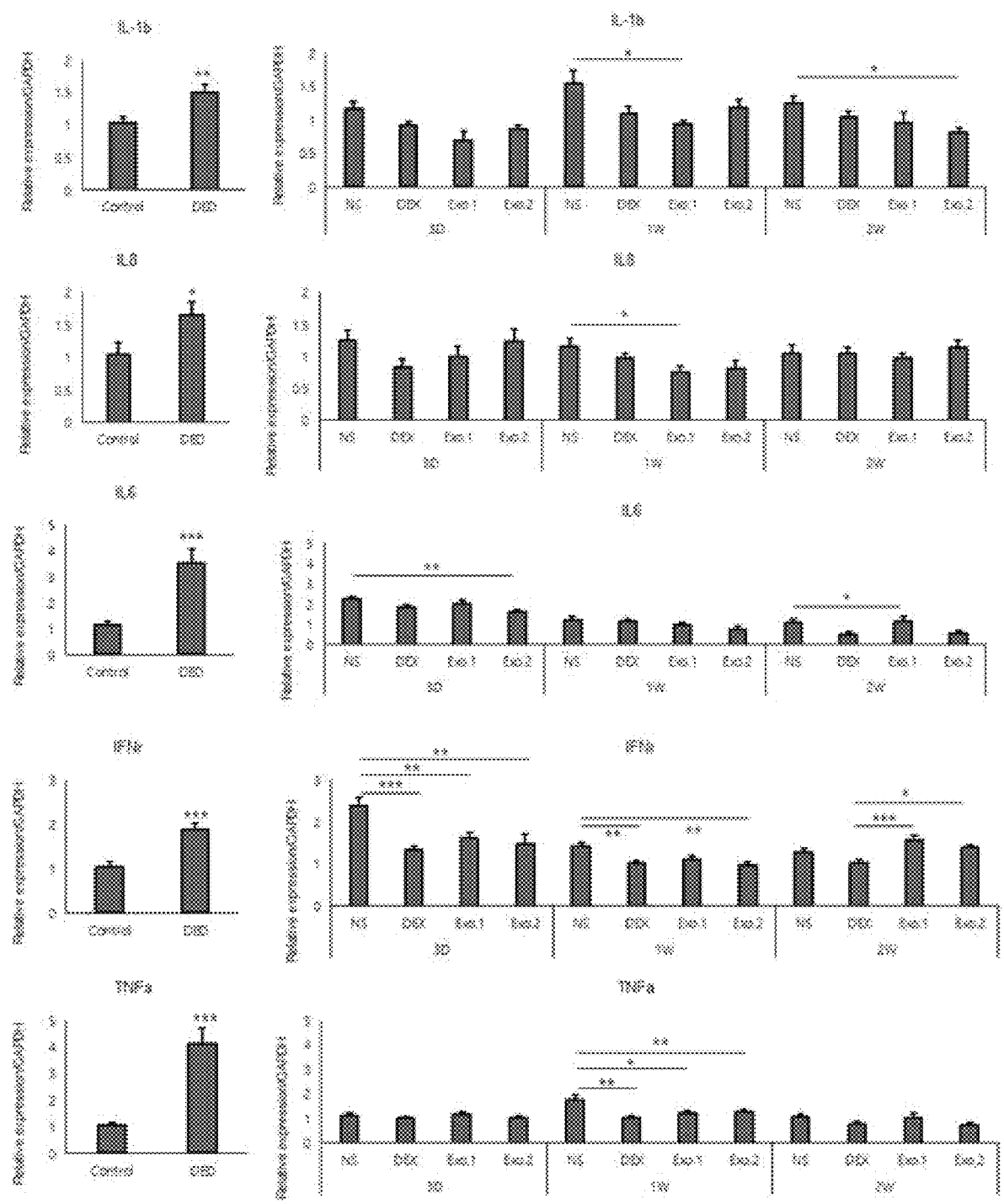
FIG. 12 shows result graphs of checking the change in cytokine secretion in the corneal tissues of an animal model with dry eye syndrome.

As a result, as shown in FIG. 12, it was confirmed that the cytokine concentration, which was high in dry eye syndrome-induced mice, was reduced by treatment with DEX and exosomes. Accordingly, it seems that exosome treatment in dry eye syndrome-induced mice affects the decrease in the cytokine secretion.

Comparative Example 1

Mesenchymal Stem Cell-Derived Exosomes

1. ELISA Assay

The human conjunctival cell line was cultured to identify whether the amniotic epithelial cell-derived exosomes and the mesenchymal stem cell-derived exosomes affect the expression of cytokines related to dry eye syndrome.

Specifically, the human conjunctival cell line cultured using a serum-free medium was maintained in a starvation state for 12 hours, and then the dry eye syndrome-like environment was induced using 70 mM of NaCl. Two hours before NaCl treatment, the amniotic epithelial cell-derived exosomes and the mesenchymal stem cell-derived exosomes were treated and cultured for 24 hours, and then the change in the concentration of IL-8 discharged out of the cells was checked. After collecting the medium used for cell culture, ELISA was performed according to the manufacturer's protocol using the LEGEND MAX™ Human IL-8 ELISA kit with Pre-coated Plates (Biolegend, San Diego, CA, USA).

Figure 13:
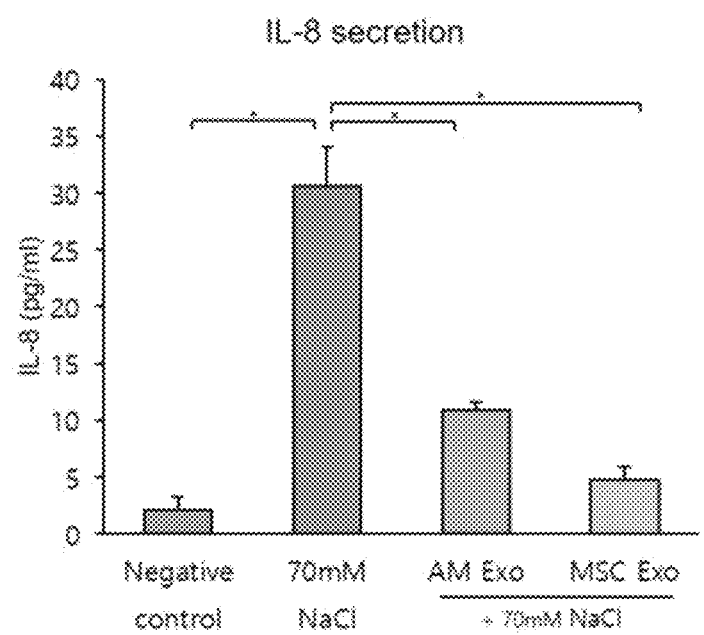
FIG. 13 is a graph comparing the concentration of IL-8 upon the treatment of exosomes derived from amniotic epithelial cells and exosomes derived from mesenchymal stem cells.

As a result, as shown in FIG. 13, it was confirmed that there was no significant difference between the expression level of IL-8, which is an inflammatory cytokine, in the dry eye syndrome model treated with the amniotic epithelial cell-derived exosomes and the mesenchymal stem cell-derived exosomes.

2. Analysis of Wound Healing

The human conjunctival cell line was cultured to identify whether the amniotic epithelial cell-derived exosomes and the mesenchymal stem cell-derived exosomes affect wound healing ability in vitro.

Specifically, when a cell confluent monolayer was formed by culturing the human conjunctival cell line in a 96-well cell culture plate inside an incubator for 24 hours, starvation state was maintained by replacement with 1% serum medium for 4 hours, and wound was formed using a wound forming tool (WoundMaker; Essen BioScience, Inc., Michigan, USA). The amniotic epithelial cell-derived exosomes and the mesenchymal stem cell-derived exosomes isolated by the method were treated, and the wound healing ability was measured through observation for 48 hours via IncuCyte (Essen BioScience, Inc., Michigan, USA).

Figure 14:
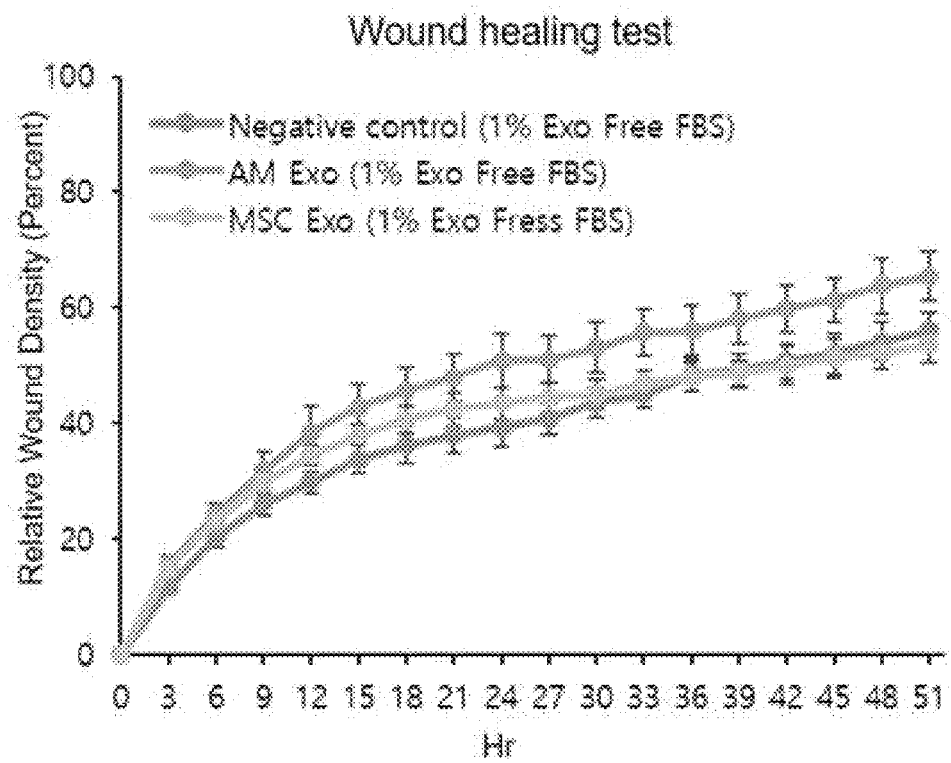
FIG. 14 is a graph comparing the wound healing ability upon the treatment of exosomes derived from amniotic epithelial cells and exosomes derived from mesenchymal stem cells.
Figure 14:
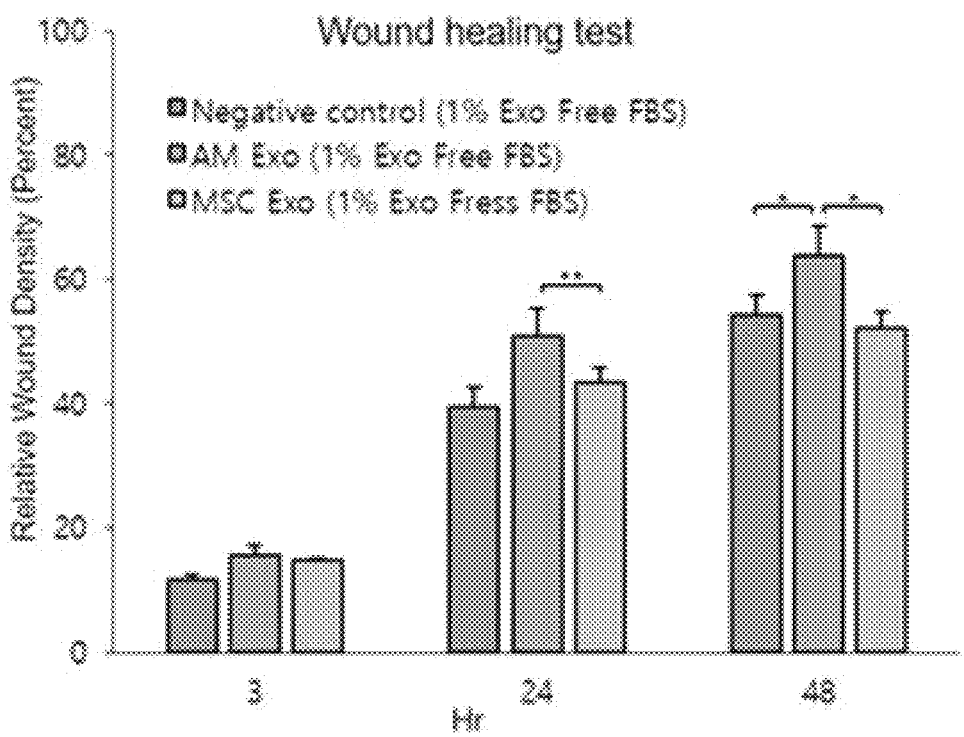

As a result, as shown in FIG. 14, there was a significant difference between the group treated with the amniotic epithelial cell-derived exosomes, the group treated with the mesenchymal stem cell-derived exosomes, and the control group, and the amniotic epithelial cell-derived exosomes showed the highest wound healing ability.

Accordingly, it was confirmed that amniotic epithelial cell-derived exosomes were more effective in treating ocular diseases than mesenchymal stem cell-derived exosomes.

Although specific parts of the present invention have been described in detail above, it is clear for those skilled in the art that these specific descriptions are merely preferred example embodiments and the scope of the present invention is not limited thereto. In other words, the substantial scope of the present disclosure is defined by the appended claims and equivalents thereof.

What is claimed is:

1. A method of treating an ocular disease, comprising:
    administering a pharmaceutical composition comprising amniotic epithelial cell-derived exosomes as an active ingredient to a subject,
    wherein the pharmaceutical composition comprising the amniotic epithelial cell-derived exosomes treats the ocular disease which is an ocular surface disease selected from the group consisting of dry eye syndrome, corneal epithelial damage, keratitis, conjunctivitis, and keratoconjunctivitis.

2. The method of claim 1, wherein the exosome has ability to heal wounds on corneal or conjunctival tissues.

3. The method of claim 1, wherein the exosome restores lacrimal gland tissues destroyed by the ocular disease, regulates goblet cells involved in stabilization of a tear film, and induces lacrimation.

4. The method of claim 1, wherein the exosome reduces secretion of an inflammatory cytokine selected from the group consisting of IL-1β, IL-8, IL-6, IFNγ, and TNFα.

5. The method of claim 1, wherein the ocular disease further comprises an intraocular disease selected from the group consisting of endophthalmitis, uveitis, and macular degeneration.

6. The method of claim 1, wherein the composition is any one formulation selected from the group consisting of eye drops, injections, granules, tablets, pills, capsules, gels, syrups, suspensions, emulsions, drops, and solutions.

7. A method of alleviating an ocular disease, comprising:
    administering a health functional food composition comprising amniotic epithelial cell-derived exosomes as an active ingredient to a subject,
    wherein the health functional food composition comprising the amniotic epithelial cell-derived exosomes alleviates the ocular disease which is an ocular surface disease selected from the group consisting of dry eye syndrome, corneal epithelial damage, keratitis, conjunctivitis, and keratoconjunctivitis.

8. The method of claim 1, wherein the ocular disease further comprises an intraocular disease selected from the group consisting of endophthalmitis, uveitis, and macular degeneration.

* * * * *